(12) United States Patent
Greenwald et al.

(10) Patent No.: US 8,337,476 B2
(45) Date of Patent: Dec. 25, 2012

(54) REAL TIME URINE MONITORING SYSTEM

(75) Inventors: Shlomo Greenwald, Ithaca, NY (US);
Zipora Greenwald, Ithaca, NY (US);
Uri Moshe Greenwald, Ithaca, NY (US)

(73) Assignee: Greenwald Technologies, LLC, Ithaca, NY (US)

( * ) Notice: Subject to any disclaimer, the term of this patent is extended or adjusted under 35 U.S.C. 154(b) by 451 days.

(21) Appl. No.: 12/544,461

(22) Filed: Aug. 20, 2009

(65) Prior Publication Data
US 2011/0046514 A1 Feb. 24, 2011

(51) Int. Cl.
*A61M 1/00* (2006.01)
*A61B 5/00* (2006.01)
*B65D 81/00* (2006.01)
*G01F 7/00* (2006.01)
*G01F 1/20* (2006.01)
*G01F 13/00* (2006.01)

(52) U.S. Cl. .......... 604/318; 600/581; 600/584; 73/216; 73/861.41; 73/197

(58) Field of Classification Search .................. 600/573, 600/574, 575, 580–582, 584; 604/317–318, 604/322–331, 346, 347, 349–353; 73/861.42, 73/861.43, 861.46, 861.65–861.68, 195, 73/197, 215, 216, 219–221, 861.41
See application file for complete search history.

(56) References Cited

U.S. PATENT DOCUMENTS

| | | | | |
|---|---|---|---|---|
| 3,650,272 A | * | 3/1972 | Ericson | 604/325 |
| 4,051,431 A | | 9/1977 | Wurster | |
| 4,099,412 A | | 7/1978 | Nehrbass | |
| 4,343,316 A | * | 8/1982 | Jespersen | 600/584 |
| 4,448,207 A | | 5/1984 | Parrish | |
| 4,457,758 A | * | 7/1984 | Norton | 604/324 |
| 4,484,582 A | | 11/1984 | Rottenberg et al. | |
| 4,554,687 A | * | 11/1985 | Carter et al. | 4/144.2 |
| 4,589,280 A | * | 5/1986 | Carter | 73/226 |
| 4,782,295 A | * | 11/1988 | Lew | 324/306 |
| 5,380,308 A | * | 1/1995 | Gunya et al. | 604/323 |
| 5,891,051 A | | 4/1999 | Han et al. | |
| 6,164,143 A | * | 12/2000 | Evans | 73/861.65 |
| 6,640,649 B1 | * | 11/2003 | Paz et al. | 73/861.41 |
| 2010/0228148 A1 | * | 9/2010 | Kim | 600/573 |

* cited by examiner

*Primary Examiner* — Max Hindenburg
*Assistant Examiner* — John Pani
(74) *Attorney, Agent, or Firm* — Brown & Michaels, PC

(57) ABSTRACT

A disposable real-time closed catheter urine output monitoring system. The monitoring system of the invention can measure urine outputs at both high and low urine flow in real time, using a pressure chamber in the form of a hollow body having an input port for coupling to a tube connected to a catheter for collection of urine from a patient, an exit port coupled to a collection container and a vent port, such that air may flow through the vent, but urine is blocked by the vent. A sensor measures flow from the exit port of the pressure chamber into the collection container, and a pressure sensor may be included to measure pressure in the pressure chamber. The invention also provides a method of using the apparatus in a real-time monitoring system.

24 Claims, 6 Drawing Sheets

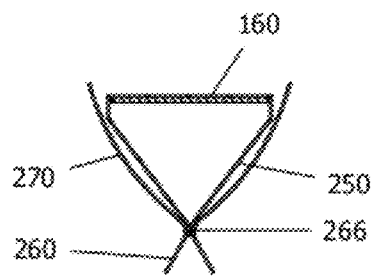
Figure 8
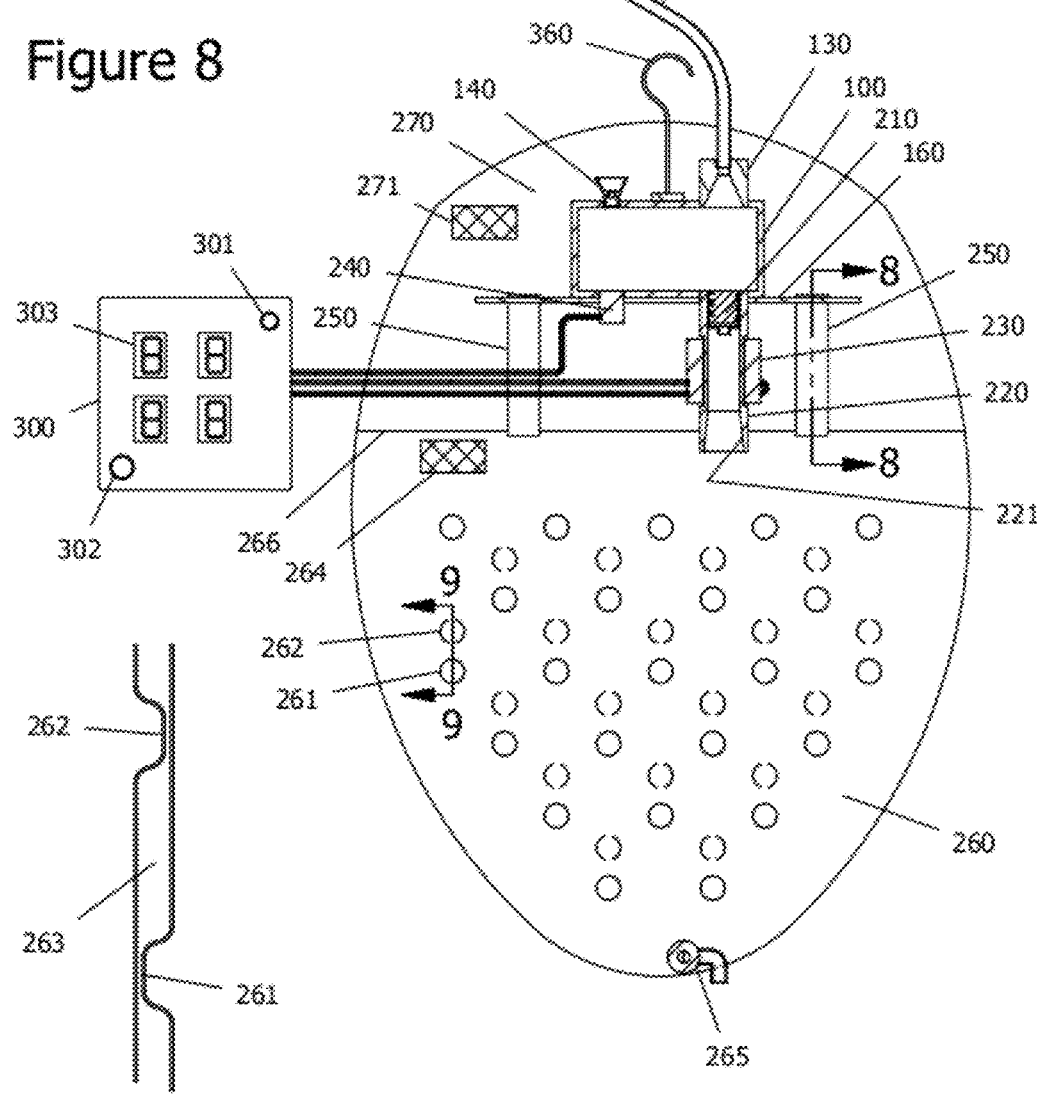
Figure 9
Figure 3

REAL TIME URINE MONITORING SYSTEM

BACKGROUND OF THE INVENTION

1. Field of the Invention

The invention pertains to medical instrumentation systems. More specifically, the invention pertains to urine measuring systems.

2. Description of Related Art

Accurate real time urine output recording is essential to patient management in both the acute and non-acute settings. The closed urine collection system currently in wide use is not automated and relies on a subjective interpretation of urine level relative to printed volumetric markings either on a rigid small volume collection tray or a larger volume collapsible collecting bag. The current system is: error prone, requires arduous physical labor to use, demands repeated potential exposures to biohazordous materials, and is inefficient.

Erroneous urine output value recordings can arise from the antiquated design of the currently widely used closed catheter system leading to improper clinical responses. These errors come most commonly in the form of subjective errors in interpreting urine volumetric markings, arithmetic errors, and neglected readings. These errors in urine output interpretation mean an incorrect patient total body volume assessment causing clinicians to over or under resuscitate their patients which may cause serious complications including renal failure, cardiovascular collapse, or pulmonary edema to name only a few.

Unnecessarily arduous time consuming labor and risk of exposure to biohazardous materials should be minimized as much as possible for medical staff caring for patients. The current urine collection system requires the medical staff member to squat or bend down at the bedside to the low position where the gravity dependent collection bag is stored, which can become quite labor intensive when repeated multiple times throughout the day. The medical staff member is also called upon to do substantial handling of the system as customarily each reading involves the interpreting staff member to pick up the collecting receptacle containing urine in order to raise the volumetric markings on the urine collection receptacle to eye level and the interpreting staff member must also raise the long plastic tube connecting the Foley catheter to the collecting bag to drive any trapped urine from the long plastic tube into the collecting bag. Thus as it now stands, the monitoring of urine output is both physically strenuous and may expose clinical staff to leaked biohazardous material due to frequent daily handling of the urine collecting receptacle and long tube.

Inefficiency is a problem with current systems, and technology providing automation of urine monitoring will bring about a great improvement in this regard. This assertion is supported strongly by a 2002 study by the American Hospital Association that nursing efficiency with non-critical care patients can be increased by as much 12 minutes per patient per day with a digital device to record and calculate hourly and daily urine outputs. With anywhere from 5 to 10 patients per nurse, this amounts to 1 to 2 hours of time saved per day per nurse. And for the critical patients where urine outputs are read and recorded much more frequently, the time savings should be even greater.

In all types of patient monitoring devices the general concept of real time measurement is a critical one. When clinicians create patient care plans the single most important determinant of the plan is the exact state of the patient at that moment in time. If the clinical data lags behind the patient's course, decisions become delayed and patients can suffer dire consequences.

With regards to urine output physiology in the catheterized patient it must be recognized that urine flow with catheterization has two extremes—both very high and very low flow. Depending on conditions, urine flow in a catheterized patient can be as high as 1-2 liters output over 2-3 minutes and as slow as 0-2 cc per hour.

Disposability is vital to a urine monitoring system. Infection control guidelines necessitate that a system for collecting patient biohazardous material such as urine must be disposed of once no longer in use. Any automated system can not forgo this important concept in patient and medical staff safety. A system with even some nondisposable components meant for re-use puts patients and hospital staff at risk of contracting hospital acquired infection.

Versatility of a urine monitoring system comes in the form of the device's ability to function in multiple positions and orientations. Patients are constantly moving and being moved in and out of their beds and rooms. Indwelling bladder catheters in effect bind the patient to the collecting system and any urine monitoring system that must remain in a fixed and rigid orientation binds or anchors the patient to a fixed position. In addition, visiting the bedside will reveal, that in real world use a urine collecting system is not often found hanging in a perfectly upright position and that the collecting bag in fact may be at any angle including entirely horizontal especially during patient transport or bed changing.

Affordability is a necessity when introducing any innovative technology with wide applications in the medical field, as resources are carefully controlled. A system that automatically measures urine output must be composed of inexpensive components to allow for low production and selling costs.

U.S. Pat. No. 6,640,649 by Paz, et al. describes an automated urine monitoring system. The system utilizes a two bag system with one bag collecting urine before passing through a drop generator, which means that this system is unable to handle medium to high urine flow in real time. Also, this system contains expensive components and thus can not practically be entirely disposable, and it requires fixation in the upright position due to the overflow conduit connecting the upper and lower bags.

Both U.S. Pat. No. 5,891,051 by Han, et al. and U.S. Pat. No. 4,448,207 by Parrish describe automated urine monitoring systems utilizing ultrasound to measure the volume of urine accumulated in a rigid collecting chamber, which limits the resolution available. The current cost of ultrasound technology would make disposal prohibitive, and the systems must remain in the fixed upright position for the ultrasound sensor to accurately measure the urine volume in the rigid collecting chamber.

U.S. Pat. No. 4,051,431 by Wurster uses urine as both a conductor of electricity and a dielectric in a capacitor to calculate its flow. This urine measuring apparatus is not designed to be a closed catheter system, but is rather a vessel into which a patient directly voids. U.S. Pat. No. 4,484,582 by Nehrbass uses a rotometer to measure flow in a closed system. Both of these are limited in accuracy at low urine flow. In addition the rotometer of Nehrbass requires a minimum pressure-head to operate which is difficult to achieve at low flow, and for the rotometer system to work, the conduit tube where the rotometer is installed must be completely full with urine which does not occur with low flow.

Jesperson's U.S. Pat. No. 4,343,316 uses an optical sensor to control upper and lower valves in a chamber of fixed volume once the urine level reaches the sensor to calculate urine output. This multi-valve system does not handle either high or low urine flow rates in real time. At high flow the rate of drainage to the collection bag will be stopped, as urine can not flow forward during the time that the chamber is emptied. The monitoring of low flow rate is delayed from real time by the time it takes to fill the chamber.

SUMMARY OF THE INVENTION

The invention provides a disposable real-time closed catheter urine output monitoring system. The monitoring system of the invention can measure urine outputs at both high and low urine flow in real time, using a pressure chamber in the form of a hollow body having an input port for coupling to a tube connected to a catheter for collection of urine from a patient, an exit port coupled to a collection container and a vent port, such that air may flow through the vent, but urine is blocked by the vent. A sensor measures flow from the exit port of the pressure chamber into the collection container, and a pressure sensor may be included to measure pressure in the pressure chamber. The invention also provides a method of using the apparatus in a real-time monitoring system.

BRIEF DESCRIPTION OF THE DRAWING

FIG. 3 shows a first embodiment of the urine monitoring system of the invention.

FIG. 6 shows a detail of the check valve, as shown in the circle labeled 6 in FIG. 1.

FIG. 7 is a bottom view of the check valve shown in FIG. 6

FIG. 8 is a cut-through section of the seal area as shown by cut line 8-8 in FIG. 3

FIG. 9 is a sectional view of two depressions, as shown by cut line 9-9 in FIG. 3.

DETAILED DESCRIPTION OF THE INVENTION

The present invention is able to record in real time both high and low flow urine outputs with the appropriate accuracy that clinicians require for decision making. At high flow rates the measurement accuracy can be within a few milliliters, while at low flow rates the accuracy can be within a fraction of a milliliter. The portion of the system which collects and measures the urine is preferably entirely disposable. Our system can be small in size and its sensors can function at different angles, which allows versatility of positioning and mobility. Our system is preferably composed entirely of inexpensive parts and can therefore be produced very inexpensively.

Figure 1:
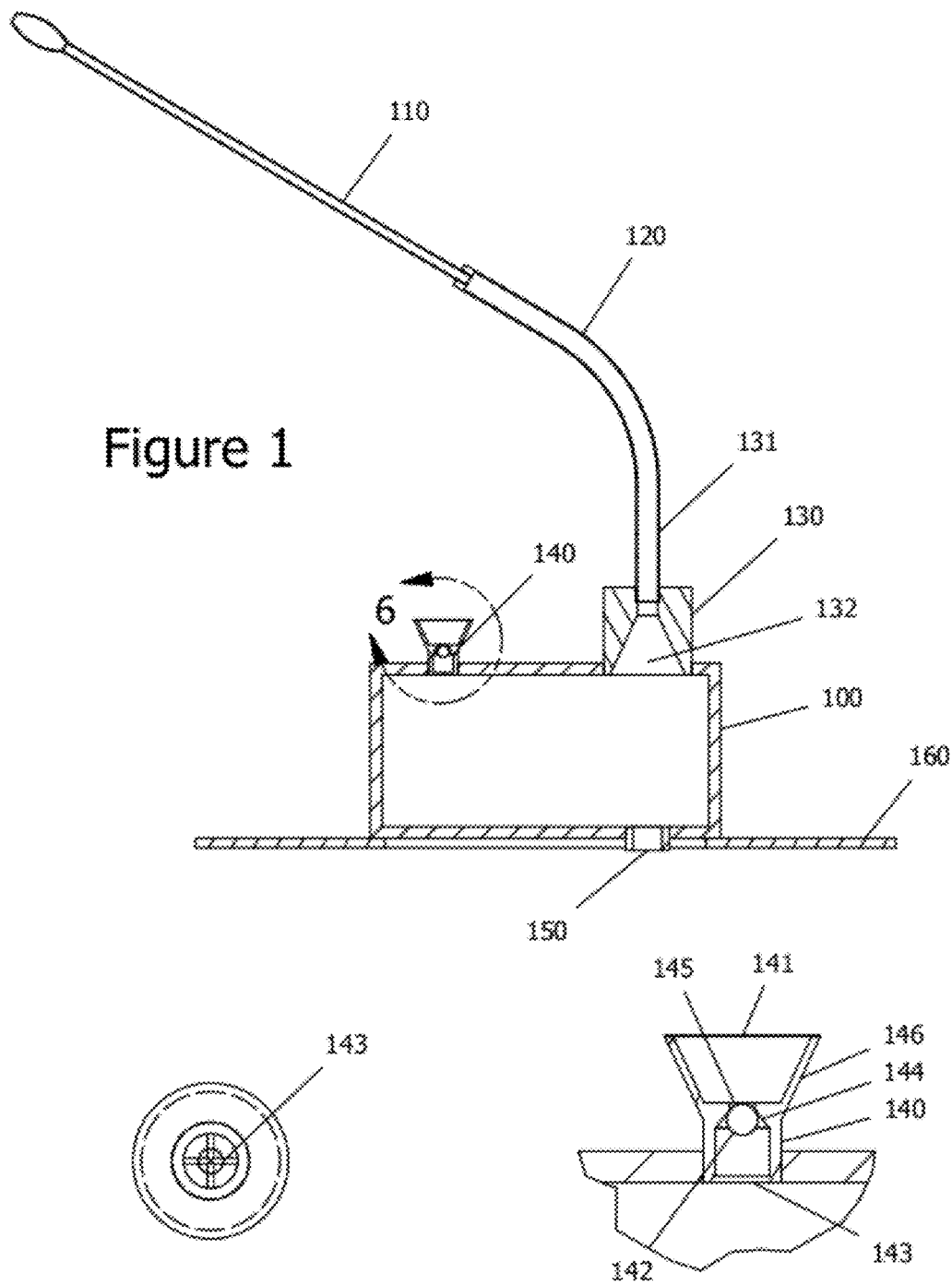
FIG. 1 shows a cross section view of the pressure chamber of the invention.
Figure 2:
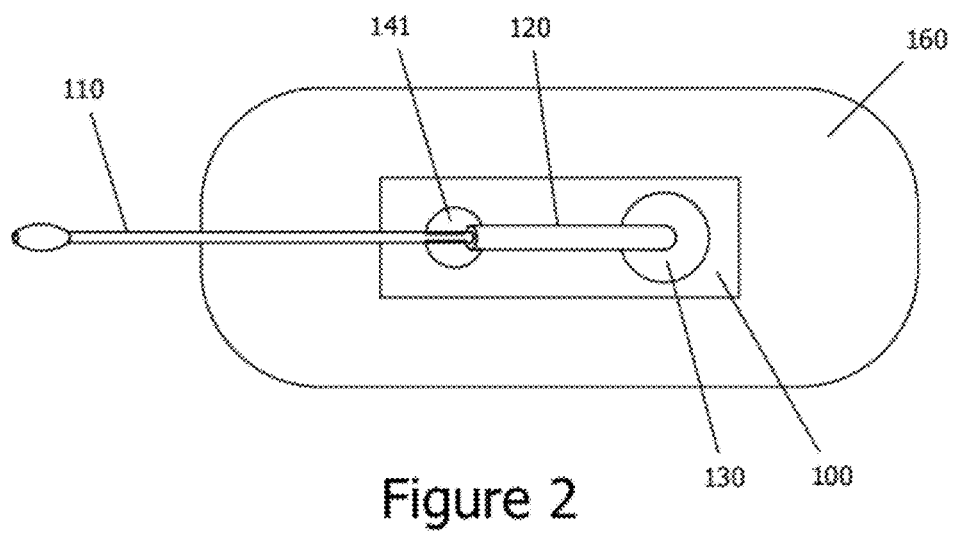
FIG. 2 is a top view of the pressure chamber.

As can be seen in FIGS. 1 and 2, a long tube 120 with a relatively large inner diameter is connected at one end to either an indwelling or external Foley catheter 110, as is standard to urine collecting systems. This long tube 120 connects at its other end to an inlet in an adaptor 130, preferably made of rigid plastic that is hollowed out inside in a shape of a frustum of a cone 132. The adaptor 130 connects to the long tube 120 via an inlet section 131 whose diameter is equal to the outer diameter of the long tube 120. This short section 131 of the rigid plastic adaptor 130 opens into the shape of a frustum of a cone 132 whose smallest diameter is equal to the inner diameter of the long tube 120. The frustum of a cone 130 then opens at its largest diameter at the outlet of the adapter, directly into the interior of the body of pressure-chamber 100, through an inlet port on its top surface, as can be seen in FIG. 1.

The rigid plastic adaptor 130 which contains the frustum of a cone shape 132 allows complete and immediate drainage of the long tube 120 at the end of a period of high urine flow. At the end of a period of high urine flow, the long tube 120 is entirely filled with urine, and the bladder is empty.

To empty the urine filled long tube 120 when the bladder is empty, air must enter into the long tube 120 from the pressure chamber 100 and displace the urine inside of the long tube 120. Were the long tube 120 to open directly to the pressure chamber 100 (without connecting first to the small rigid adapter 130 with the frustum of a cone inner shape), urine would form a drop like surface at the opening of the long tube because of surface tension effect, and this drop shaped surface would block passage of air up into the long tube 120 from the pressure chamber 100.

One method to alleviate this problem is to cut the end of the long tube 120 at an angle, typically 30 to 45 degrees, so the opening at the end is larger then the tube diameter. This method still relies on gravity force to overcome the surface tension, so it is most effective when the system is hanging vertically.

The frustum-of-a-cone shaped adaptor 132 works to limit the formation of the drop like surface and allows passage of air up into the long tube 120. When urine passes from the long tube 120 into the frustum of a cone shape 132, the urine is drawn down along the surface of the frustum of a cone shape 132 due to capillary forces between the urine and the surface of the frustum of a cone 132. The urine then runs down the sides of the frustum of a cone 132 towards its wide mouth which is a few times the diameter of the long tube 120. This wide diameter of the mouth of the frustum of a cone 132, will not allow the formation of a drop shaped surface of urine across the larger diameter opening. Air from the pressure chamber 100 freely rises up into the long tube 120 draining the long tube 120 immediately into the pressure chamber 100. Without this there might be a significant period of urine stasis inside of the long tube 120. Stagnant urine filling the long tube 120 is a significant risk for acquired urinary tract infections as bacteria introduced from the environment are provided a direct path of travel into the patient's urinary system through retrograde travel up the column of stagnant urine in the long tube 120.

The pressure-chamber 100 is a small rigid chamber typically of a rectangular shape with a volume of 20-40 cc and whose inner height is typically less than 1 inch.

On the top surface of the pressure-chamber 100 there is a vent port having a selective vent, here shown in the form of a zero pressure V-ball type check valve 140 intended to allow air flow in and out of the chamber 100 while not allowing urine to pass out to the environment. Details of this check valve arrangement are shown in FIGS. 6 and 7. In some cases the pressure box will have two vent ports located at opposite corners. This will ensure that if the system is lying horizontally, during low urine flow, only one vent at a time would be covered in urine while the other would be open to the passage of air. It will be understood that other forms of vent which would allow air flow while blocking urine would also be appropriate within the teachings of the invention.

Very small amounts of urine may infrequently leak past the vent especially when the system is in the horizontal position, and for those rare cases of leakage of urine past the check valve 140, a bidirectional membrane 141 is placed on the top surface of the check valve 140 to allows only air flow in and out of the pressure chamber 100 while not allowing urine to pass out into the environment. To prevent this membrane 141 from saturating with urine, and having a sufficient air flow rate, the membrane 141 must have a large enough functional area, so the membrane 141 is placed on the top surface of a frustum of a cone 146 that flares out from the walls of the check valve 140 and whose largest diameter opens away from the check valve 140 towards the outside of the system. Membrane 141 may be made of expanded polytetrafluoroethylene (ePTFE) liner vent material such as is available from W. L. Gore & Associates, Inc.

The check valve 140 may be of any of the numerous check valve designs known to the art. A preferred embodiment is of the V-ball type which contains a floating check element such as a ball 142, as shown in FIG. 1. At its open position, the ball 142 rests on grid 143 as is shown in FIG. 7, and at its closed position the ball 142 is pushed upwards by either urine or air into the 'V' shaped part of the V-ball type check valve 144 to seal the exit hole 145 as can be seen in FIG. 6. A floating ball which can be used with the check valve 140 of the invention is commercially available from Precision Plastic Ball Company of Franklin Park. Ill.

At the bottom surface of the pressure chamber 100 there will be an exit port 150 as can be seen in FIG. 1.

In a first embodiment of the urine output monitoring system, as shown in FIG. 3, the exit port 150 of the pressure chamber 100 will be fitted with a rigid short tube 220 and a second opening at the bottom of the pressure chamber 100 will be fitted with a small pressure sensor 240. A nozzle 210 is fitted into the top part of the short rigid tube 220 and drains urine from the pressure-chamber 100 directly into the short rigid tube 220. Typically the length of the short rigid tube 220 will be a few inches long, with an inner diameter of ⅜ of an inch and an outer diameter of less than one inch.

A low flow sensor 230 is mounted on both sides of the short rigid tube 220 adjacent to the lower surface of the pressure chamber 100. This sensor is preferably an RF energy type sensor as described in U.S. Pat. No. 7,482,818 or U.S. Pat. No. 8,049,517, which are incorporated herein by reference. It will be understood, however, that other sensors might be used within the teachings of the invention.

The output of the pressure gauge 240 and low flow sensor 230 are connected to a controller 300 with a digital display 303 and indicator 301. One or more control switches 302 may be included on the controller. The controller is preferably microprocessor based.

The bottom end of the short rigid tube 220 flares out into a cone 221, which opens to a large collapsible collecting bag 260. Typically the volume of the collecting bag 260 is 2-2.5 litters. At least one bi-directional membrane 264 to serve as an air vent will be located at the top of the front or back surface of the collecting bag 260. At the bottom of the collecting bag 260 will be a standard drain valve 265 for the purpose of emptying the urine. Bi-directional membrane 264 may be made of expanded polytetrafluoroethylene (ePTFE) liner vent material such as is available from W. L. Gore & Associates, Inc.

In order to prevent the front surface of the collecting bag 260 from sticking to the back surface when a thin layer of urine coats both sides, small depressions 261 and 262 are made in the front and back surfaces of the collapsible collecting bag 260 such that when the bag is emptied, a gap 263 will be maintained and the urine will be able to fully pass through the collecting bag. This is shown in detail in FIG. 9.

The liquid-tight seal 266 separates the collapsible bag 260 and a small closed pocket 270 that encloses the pressure chamber 100 and the sensors. A bi-directional membrane 271 to serve as an air vent is located at the top of the front surface of the closed pocket 270. Bi-directional membrane 271 may be made of expanded polytetrafluoroethylene (ePTFE) liner vent material such as is available from W. L. Gore & Associates, Inc.

Hook 360 will allow hanging of the urine collecting bag 260 to the bed frame and is typically mounted at the center of the top surface of the pressure chamber 100, as can be seen in FIG. 3.

As is shown in FIG. 8, one end of each of the two straps 250 is fastened to base plate 160 (one on each side) and the other end of each strap is fused together with the liquid tight seal 266. The main purpose of the two straps 250 is to transfer the weight of the urine collecting bag 260 to the base plate 160 which is rigidly connected to the pressure chamber 100, and from there the weight is transferred to the rigid hook 360.

Figures 4, 10:
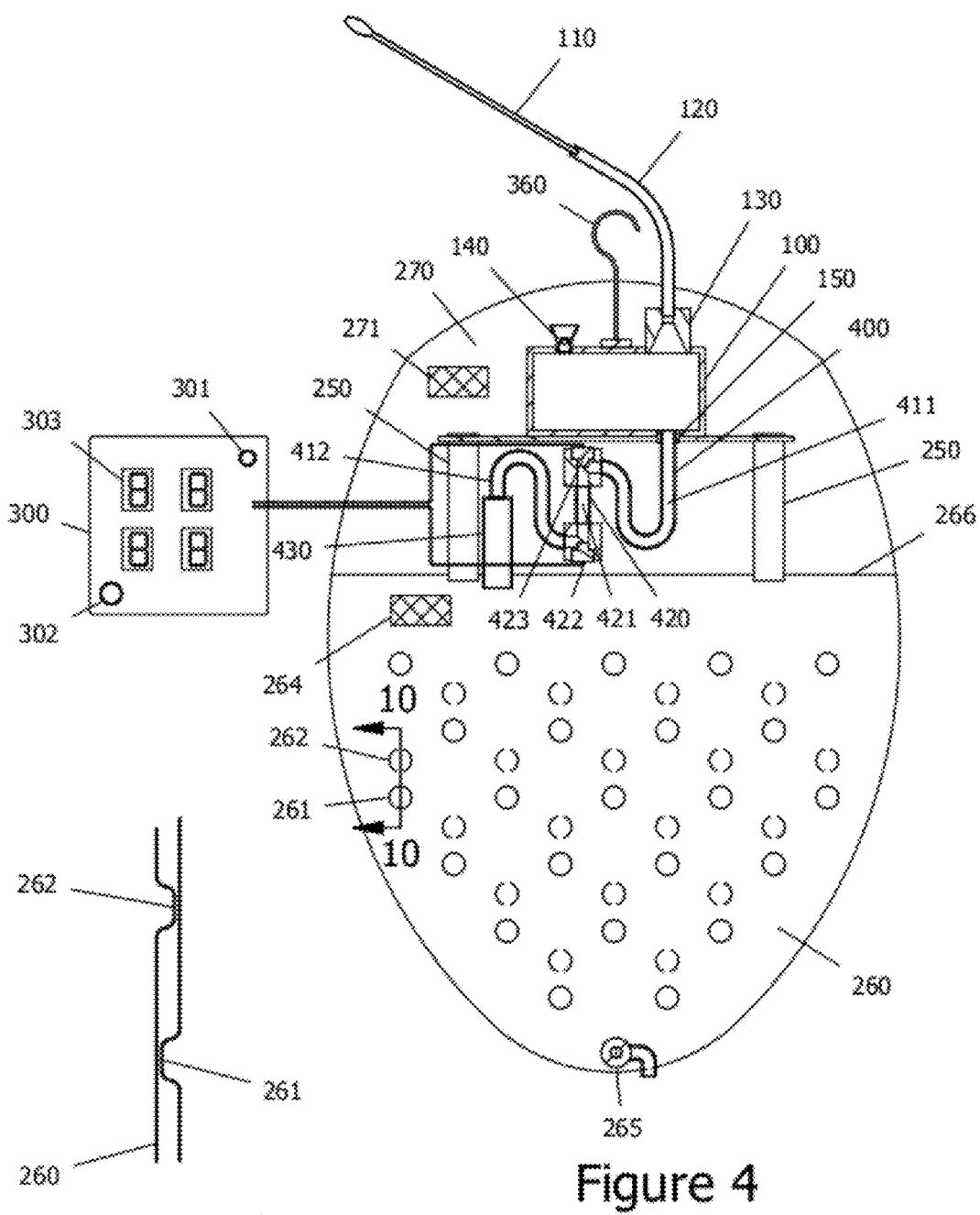
FIG. 4 shows a second embodiment of the urine monitoring system of the invention.
FIG. 10 is a sectional view of two depressions, as shown by cut line 10-10 in FIG. 3.

In a second embodiment, as is shown in FIG. 4, the exit port 150 at the bottom of the pressure chamber 100 is fitted with a small opening that will drain directly into a conduit 400 coupled to an ultrasonic flow sensor 420. The conduit 400 consists of a capillary tube 411, 421 and 412 shaped like the letter "W" with the last arm 412 of the "W" shape attached to a larger diameter rigid tube 430 that will break capillary flow and drain into the collecting bag 260. A conduit with only two capillary tubes shaped like a "V", or three capillary tubes shaped like a rotated S, can also be used within the teachings of the invention, and other arrangements are possible.

In this embodiment, conduit 400 has five arms all together: four arms shaped in a "W" with capillary flow, and a fifth arm 430 with regular flow. Preferably, the ultrasonic flow meter 420 will be located on the third arm 421 of the "W" shape, although other placements on other arms of the "W" are possible.

Typically the height of the "W" shaped conduit 400 will be of the order of 1-1.5 inches. The inner diameter of the capillary tube 411 and 412 will be typically of the order of ⅛ inches. The inner diameter of the large diameter rigid tube 430 will be typically of the order of ½ inches. Typically the diameter of the ultrasonic meter channel 421 will be of the order of 3/16-¼ inches.

Ultrasonic transducers 422 and 423 will be facing each other and immersed in the urine. One transducer 423 is mounted at the top of the third arm 421 of the "W" while the other 422 is mounted at the bottom, and the transducers are coaxial with the urine flow direction.

Capillary flow in this type of conduit will maintain only urine in the channel of the ultrasonic flow meter 420 at all times, which is beneficial to achieve accurate fluid volume measurements and resolutions using this type of flow meter. The conduit 400 will not interfere with the innate urine flow of the Foley catheter system because of the use of pressure-chamber 100. The four arms of the "W" will allow for flow of urine through the capillary tubes 411, 412 and 421 to travel at a sufficient rate at low urine flow to achieve the necessary resolution. The fifth arm 430 of large diameter will break capillary flow so as not to draw urine out of the "W" by inertia. The capillary flow in the conduit 400 is not affected by the position of the entire system. Even when there is no urine flow through the system, the conduit 400 maintains urine in the "W" shape through capillary forces independent of the position of the system so that no air ever passes through the ultrasonic flow meter.

The use of an ultrasonic flow sensor 420 in this secondary embodiment will directly measure both high and very low urine flow in real time, as opposed to devices which do not measure flow directly, but rather use ultrasonic sensors to measure the height of a volume of urine in a rigid collecting container. The ultrasonic flow meter 420 employed in the second embodiment is a directly immersed, time of flight, coaxial, ultrasonic flow meter. Using this type of directly immersed ultrasonic flow meter gives high accuracy, potentially of greater than 1%.

The pressure chamber 100 enables the use of a flow measuring sensor to measure real time urine output without interfering with the innate physiological urine flow.

Figure 5:
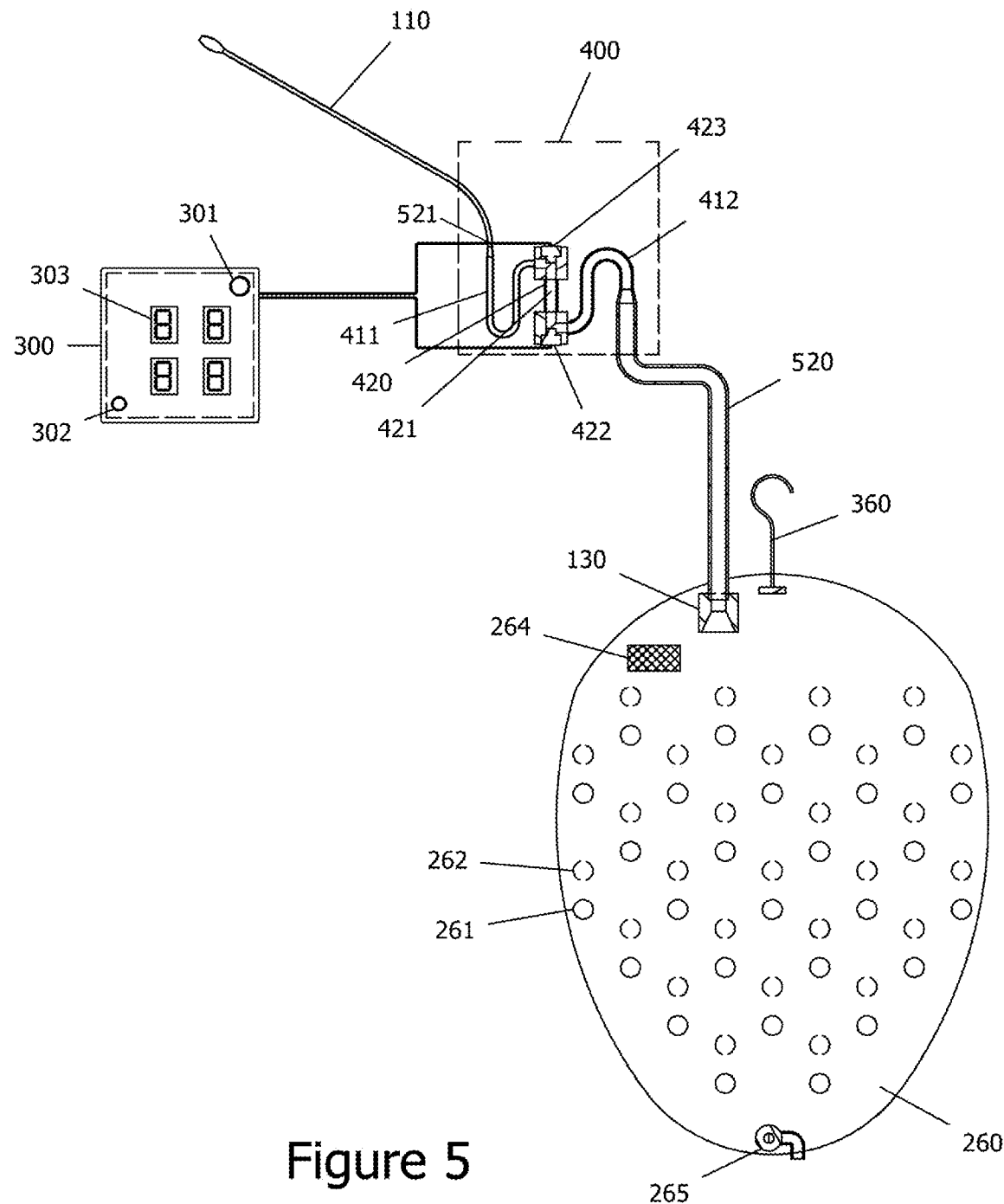
FIG. 5 shows a third embodiment of the urine monitoring system of the invention.

In a third embodiment, the 'W' shaped conduit 400 together with the ultrasonic flow sensor 420 directly between a catheter connector 521 into which is plugged a Foley catheter 110 and long tube 520, without the use of a pressure chamber, as can be seen in FIG. 5. The Foley catheter 110 itself is a capillary tube due to its narrow diameter and only passes urine and no air into the 'W' shaped conduit 400. As was explained above the W shaped conduit will maintain liquid in the ultrasonic flow meter channel at all times which is essential for obtaining accurate measurements. Also the W conduit allows optimizing the ultrasonic flow meter channel 421 diameter and material to achieve the needed accuracy for the high flow and low flow.

Figure 11:
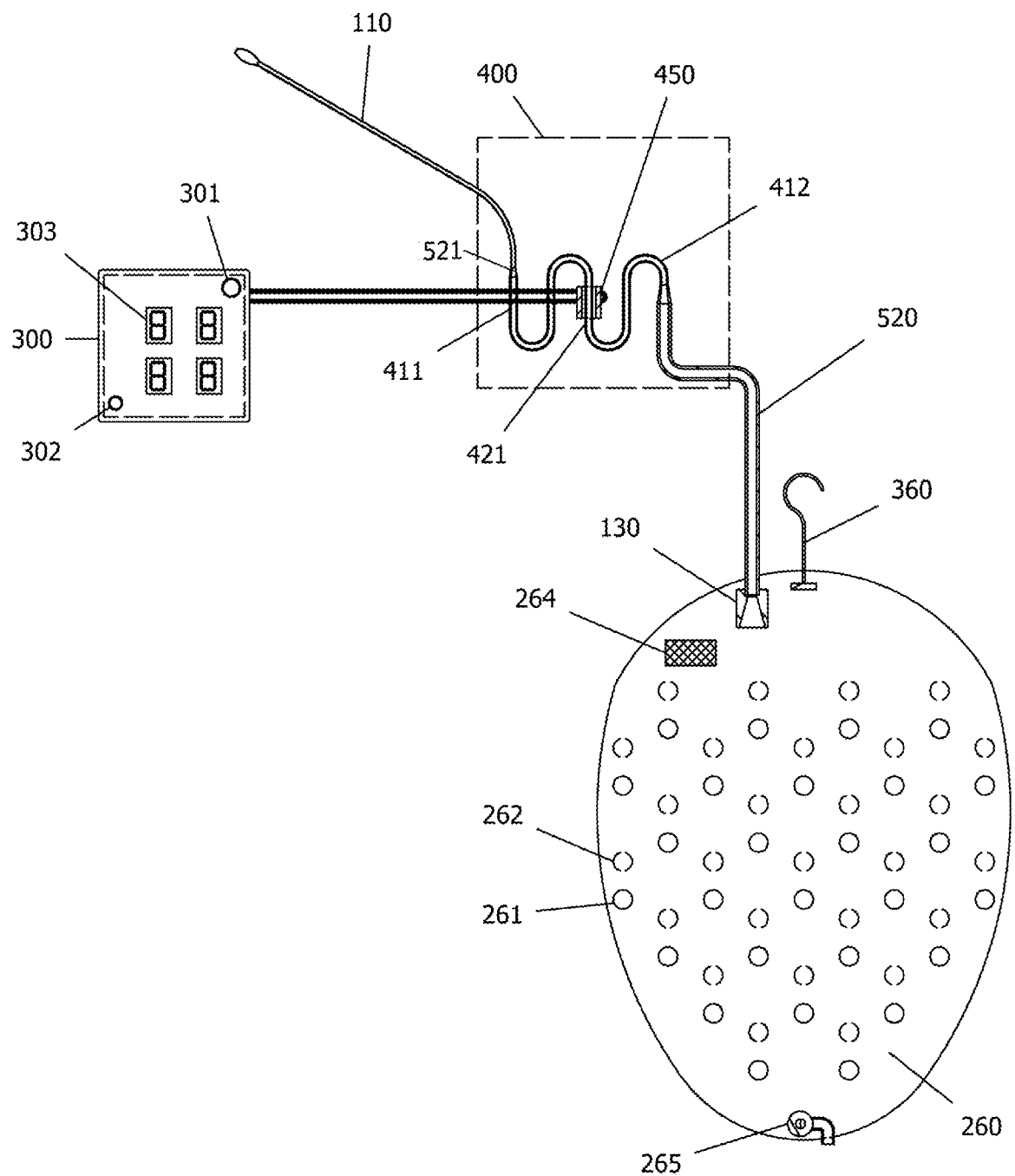
FIG. 11 shows a fourth embodiment of the urine monitoring system of the invention.

In a fourth embodiment, as can be seen in FIG. 11, an external "clamp-on" ultrasonic flow-meter 450 is located on one of the W arms. The W shaped conduit 400 will maintain liquid in the ultrasonic flow meter channel 421 at all times which is essential for obtaining accurate measurements. Also the W conduit 400 allows optimizing the ultrasonic flow meter's channel 421 diameter, material and wall thickness to achieve the needed accuracy for the high flow and low flow.

It is possible to place a clamp-on type ultrasonic flow meter directly on the Foley catheter 110, which is of small inner diameter and functions as a capillary tube, before it connects to the long tube 520. However, this method is not preferred because a) air can enter into the end of the catheter due to patient movement, b) the Foley catheter tube diameter, wall thickness and material are not optimized for the clamp-on ultrasonic flow meter.

Principles of Operation

Physiologically, a patient with a urine drainage catheter can produce urine at both high and low rates of flow as described earlier. When there is high urine flow in the system the following will all occur: Urine travels from the patient through the Foley catheter 110 into the long tube 120 entirely filling the long tube 120 and driving the air previously in the Foley catheter 110 and the long tube 120 into the pressure-chamber 100.

The behavior of the pressure chamber 100 with high urine flow has three phases:

Phase I: Filling the Pressure-Chamber

The pressure in the pressure-chamber 100 rises above atmospheric pressure due to the incoming air from the Foley catheter 110 and long tube 120, and forces air out mainly through the check valve 140 with a small amount of air passing through the exit port 150 before it is covered with urine. This release of air from the pressure-chamber 100 allows the pressure in the pressure-chamber 100 to equilibrate with atmospheric pressure and thus maintains a pressure gradient that favors urine flowing at a high rate into the pressure-chamber 100 from the long tube 120.

As urine enters the pressure-chamber 100 from the long tube 120, the pressure-chamber 100 is draining urine through the exit port 150 into the collecting bag 260 via the nozzle 210 and tube 220 in the first embodiment or the "W" shaped conduit 400 in the second embodiment.

The rate of flow of urine through the exit port 150 is at a much slower rate then that of the rate of urine flow into the pressure chamber 100 from the long tube 120. The rate of drainage of urine through the exit port 150, in this phase, is determined by the nozzle 210 or W-shaped conduit 400 characteristic and the pressure generated by the height of urine in the pressure-chamber 100 which is being filled by the long tube 120.

Phase II: Full Chamber

Once the urine in the pressure-chamber 100 entirely fills the chamber to its top, all the air in the pressure chamber 100 will be pushed outside of the pressure chamber 100 into the environment through the check valve 140. When urine reaches it, the V-ball 142 will seal the check valve 140, and the pressure in the pressure-chamber 100 will increase rapidly.

Because the pressure chamber 100 and long tube 120 are now filled only with urine, a noncompressible liquid, and no air, in this phase the nozzle 210 or the W shaped conduit 400 is suddenly acted upon by a transmitted pressure which can be calculated as the bladder pressure minus the pressure decrease across the length of the narrow tube Foley catheter 110, plus the pressure due to the height difference between the bladder and pressure-chamber 100.

This rapid increase in pressure suddenly acting on the nozzle 210 or the W shaped conduit 400 causes a rapid increase in the rate of drainage through the nozzle 210 or the W shaped conduit 400 into the collecting bag 260. This high flow through nozzle 210 or the W shaped conduit 400 will continue until the bladder is empty.

Phase III: Bladder is Empty

Once the bladder is emptied, there will be no urine coming into the long tube 120 from the bladder to displace the urine inside the long tube 120 into the pressure-chamber 100, nor is there air in the pressure chamber 100 at this time to rise and displace urine in long tube 120 either. Physics principles will not allow urine to be displaced by a vacuum, but even so urine will continue to flow through the nozzle 210 or the W shaped conduit 400 due to the principle of inertia of flow. This will cause the pressure in the chamber 100 to fall below atmospheric pressure which will cause the V-ball 142 of the check valve 140 to be pushed down into an open position allowing air to enter the pressure chamber 100.

At this point, with air again in the pressure chamber, the flow rate through the nozzle 210 or the W shaped conduit 400 is determined again mainly by the urine's height in the pressure-chamber 100. This is a relatively slower rate of drainage and depending on the embodiment, flow at this time will either be discrete through the nozzle 210 or very low flow rate through the W shaped conduit 400.

Urine that drains from the pressure-chamber 100 is replaced by air coming in through the open check valve 140. The air in the pressure-chamber 100 has a tendency to rise to the highest point in the system which is through long tube 120 displacing the urine in the long tube 120 and allowing it to drain into the pressure-chamber 100 by gravity.

Of note, were the type of V-ball 142 used substituted for a very light weight ball, the behavior of the system would change and this may be advantageous. A very light V-ball 142 will be pushed up into the closed position by the air driven into the pressure chamber 100 from the long tube 120 and out from the pressure chamber 100 through the v-ball check valve 140 in Phase I rather than urine when its completely fills the pressure chamber 100. This will allow the pressure in the pressure chamber to build at a faster rate since the urine does not have to fill the pressure chamber 100 to the top to close the check valve 140.

During low urine flow, urine will only partially fill the pressure chamber 100 and the V-ball check valve 142 will remain open. The flow rate through the exit port 150 is determined by the height of the fluid in the pressure chamber 100 and the flow characteristic of the nozzle 210 or the W shaped conduit 400.

Principles of Measurement

In the first embodiment as shown in FIG. 3, high urine flow in the system is measured by the pressure sensor 240. Since the pressure in the collecting bag 260 is atmospheric pressure, the pressure measured by the pressure sensor 240 is the pressure gradient across the nozzle 210. Using the pressure measured across the nozzle 210 combined with the nozzle's 210 measured calibrated constant (Cv) allows for the calculation of the flow rate (dq/dt) which is given by:

$$dq/dt = Cv \times \sqrt{P(t)} \qquad \text{eq. [1]}$$

Because the time constant of the pressure sensor 240 is of the order of one millisecond, we are measuring the pressure P very frequently (preferably 10-20 times per second). We can use the above formula to calculate the volume of urine by numerical integration done by the microprocessor using the following formula below where (Δq) is a small volume drained over the brief interval (Δt), and P(Δt) is the measured pressure during this time:

$$\Delta q = Cv \times \sqrt{P(\Delta t)} \times \Delta t \qquad \text{eq. [2]}$$

When there is low urine flow in the system the pressure in the pressure-chamber 100 will always equal atmospheric pressure, as described before, and gravity is the main force driving urine through the nozzle 210. In this case of low urine flow, flow through the nozzle 210 will be discrete and is determined by the urine height in the pressure chamber 100.

Low urine flow will be measured with the low flow sensor 230 which is able to count units of discrete flow. Knowing the nozzle's 210 premeasured characteristics we know the number of units of discrete flow that equal one milliliter. Counting units of discrete flow and then translating the total to milliliters gives the total volume of urine drained under low flow.

The microprocessor will integrate readings from the two sensors.

Low flow sensor 230 also has the ability to discern continuous flow from discrete flow, and combined with measurements from the pressure sensor 240 the following can take place:

1) When the microprocessor has a signal of elevated pressure from the pressure sensor 240 and a signal of continuous flow from the low flow sensor 230 it means that there is a high flow state in the system and it will use the above mentioned equation [2] to calculate the urine volume drained into the collecting bag 260.

2) When the microprocessor receives a signal of low pressure from pressure sensor 240 and a signal of discrete flow from the low flow sensor 230 it signifies a low flow state and the system will count units of discrete flow and convert the tally to the urine volume drained into the collapsible bag 260.

3) When the microprocessor receives a signal of low pressure from pressure sensor 240 and a signal of continuous flow from the low flow sensor 230 this is caused by the system lying in the horizontal position and a full collecting bag 260 spilling back flow of urine into short rigid tube 220. In this case an audible alarm will sound and no further volumes will be tabulated.

Due to properties of the high flow sensor 240 and the low flow sensor 230 the system need not be in a fixed position and allows for movement in all three planes. The high flow sensor 240 and the low flow sensor 230 are able to function at a lateral/side-to-side or an anterior-posterior/front-to-back tilt.

The advantage of this feature is that when the system is haphazardly hung at the bedside, the system will still function, and if lying in the horizontal the system will function until the collecting bag 260 fills with urine and there is back flow into the short rigid tube 220 which will sound the audible alarm.

To ensure maintenance of a an angle at which the low flow sensor 230 will still function in the horizontal position the rigid pressure-chamber 100 will have a wide base 160, as can be seen in FIG. 2, so that when the system is lying in the horizontal position low pressure sensor 230 will be at an angle to the horizontal plane that will allow it to function.

In the second embodiment as shown in FIG. 4, during high urine flow the pressure in the pressure-chamber 100 will increase, as explained above, causing a high urine flow rate through the "W" shaped conduit 400 and through the ultrasonic meter channel 421. During low urine flow the pressure in the pressure-chamber will be equal to atmospheric pressure and the flow rate through the "W" shaped conduit 400 will be determined by the urine height in the pressure-chamber 100. The inner diameter of the ultrasonic meter channel 421 is such that even at very low flow the velocity of the urine is high to allow the resolution and accuracy that is needed.

By knowing the cross sectional area A of the flowmeter channel 421 and the velocity of the urine as measured by the ultrasonic flowmeter 420, the volume of urine can be calculated numerically using the formula:

$$\Delta q = A \times v(t) \times \Delta t \qquad \text{eq. [3]}$$

Where; v(t) is the average velocity during the very short time Δt.

The ultrasonic flowmeter 420 is able to discern between a forward flow and a backward flow. If lying in the horizontal the system will function until the collecting bag 260 fills with urine and there is back flow which will sound the audible alarm.

The urine monitoring system will have a digital display 303 which will have the following features:

1) It will display the urine output of the last 60 minutes, which display will be updated periodically.
2) It will display the total urine output of the last 8 hours, which display will be updated periodically.
3) It will display the total urine output of the last 24 hours, which display will be updated periodically, preferably at least every hour.
4) It will display the total urine output of each hour of the 8 elapsed hours before the last hour
5) It will display the time from the moment the Foley catheter was installed, preferably in units of days and hours.
6) Flash an indicator, preferably a small segment on the display or a light, when there is a urine flow.
7) Preferably, the monitor will be turned on just before the catheter is installed, and will not be turned off while it is installed.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A urine collection monitoring system comprising:
   a) a pressure chamber, comprising:
      i) a hollow body having an input port for coupling to a tube connected to a catheter for collection of urine from a patient, an exit port and at least one vent port;
      ii) a vent located at the vent port, such that air may flow through the vent, but urine is blocked by the vent;
   b) a flow sensor for measuring a quantity of urine flowing from the exit port of the pressure chamber at both a continuous flow and a discrete flow wherein the flow sensor is configured to measure: (i) the quantity flowing at the continuous flow, based upon a pressure in the hollow body, and (ii) the quantity flowing at the discrete flow, by counting discrete units of fluid flowing from the exit port;
   c) a urine collection container coupled to the exit port of the pressure chamber; and
   d) a controller having an input coupled to the flow sensor.

2. The system of claim 1, further comprising an adaptor located at the inlet port of the hollow body, having an inlet for coupling to the tube, and an outlet opening into the hollow body through the inlet port.

3. The system of claim 2, in which the outlet of the adaptor is in the form of a frustum of a cone having a diameter which increases from the inlet to the outlet.

4. The system of claim 2, further comprising a catheter coupled to the inlet of the adaptor by a tube.

5. The system of claim 1, further comprising a nozzle connected to the exit port of the pressure chamber.

6. The system of claim 1, in which the vent comprises a check valve having a floating check element which floats into a blocking position in the presence of liquid, in which the floating check element blocks the vent, preventing urine flow through the vent.

7. The system of claim 6, in which the check valve comprises a v-shaped seat, the floating check element is a ball, and the blocking position is a position in which the ball floats into the v-shaped seat to seal the check valve.

8. The system of claim 1, in which the vent further comprises a bidirectional membrane on an outlet of the vent that permits air to flow through the vent, but limits urine leakage from the outlet of the vent.

9. The system of claim 1, in which the urine collection container is a collapsible urine collection bag.

10. The system of claim 9, in which the urine collection bag further comprises a plurality of depressions on a surface, such that when the bag is empty, a gap will be maintained and urine will be able to fully pass through the collecting bag.

11. The system of claim 9, in which the urine collection bag further comprises a bidirectional air membrane for venting air into and out of the bag.

12. The system of claim 1, in which the urine collection container further comprises a drain valve for emptying the container.

13. The system of claim 1, in which the pressure chamber is enclosed in a pocket in the urine collection container.

14. The system of claim 1, in which the controller comprises a microprocessor.

15. The system of claim 14, in which the microprocessor is programmed to collect flow data from the flow sensor over time, and to integrate the flow data to measure urine output.

16. The system of claim 14, wherein the flow sensor comprises a pressure sensor having an input coupled to the hollow body, and an output providing pressure data representing pressure measured at the input, and in which the microprocessor is programmed to collect the pressure data from the output of the pressure sensor over time, to derive flow data from the pressure data and a diameter of the exit port, and to integrate the flow data to measure high flow urine output.

17. The system of claim 14, in which the flow sensor comprises:
   a high flow sensor comprising a pressure sensor having an input coupled to the hollow body and an output providing pressure data representing pressure measured at the input; and
   a low flow sensor adjacent to the exit port, having an input for detecting discrete flow from the exit port, and an output providing flow data representing units of discrete urine flow from the exit port when urine flow from the exit port is a discrete flow and providing a continuous flow indication when urine flow from the exit port is a continuous flow;
   the microprocessor being programmed to collect the pressure data from the output of the high flow sensor over time, to derive flow data from the pressure data and a diameter of the exit port, and to integrate the flow data to measure high flow urine output;
   the microprocessor being further programmed to collect the flow data representing units of discrete urine flow from the low flow sensor over time, and to integrate the units of discrete urine flow to measure low flow urine output,
   the microprocessor being programmed to recognize a high flow state from an elevated pressure indication on the pressure data from the pressure sensor and an indication of continuous flow from the low flow sensor,
   the microprocessor being programmed to recognize a low flow state from a lower pressure indication on the pressure data from the pressure sensor and a flow data comprising units of discrete urine flow from the low flow sensor;
   the microprocessor being programmed to use the high flow urine output during a high flow state and the low flow urine output during a low flow state; and
   the microprocessor being programmed to combine the low flow urine output and the high flow urine output determine a total urine output.

18. The system of claim 14, further comprising a display under control of the microprocessor.

19. The system of claim 18, in which the microprocessor is programmed to display at least urine output as a function of time.

20. The system of claim 19, in which the microprocessor is programmed to display total urine output over a selected period of time, which is updated periodically at a selected time interval.

21. The system of claim 20, in which the microprocessor is programmed to display the total urine output of each hour of a selected number of previously elapsed hours.

22. The system of claim 18, in which the microprocessor is programmed to display elapsed time since the catheter was connected to the system.

23. The system of claim 1, further comprising an indicator which is activated when the system detects urine flow.

24. The system of claim 1, in which the flow sensor comprises an RF energy type sensor surrounding a tube coupled to the exit port of the pressure chamber.

* * * * *

UNITED STATES PATENT AND TRADEMARK OFFICE
CERTIFICATE OF CORRECTION

PATENT NO. : 8,337,476 B2  Page 1 of 1
APPLICATION NO. : 12/544461
DATED : December 25, 2012
INVENTOR(S) : Greenwald et al.

It is certified that error appears in the above-identified patent and that said Letters Patent is hereby corrected as shown below:

Claim 1, (Column 12, line 43): Add the word --to-- after the word "output".

Signed and Sealed this
Nineteenth Day of February, 2013

Teresa Stanek Rea
*Acting Director of the United States Patent and Trademark Office*